US00PP32709P2

(12) United States Plant Patent
Beekenkamp

(10) Patent No.: US PP32,709 P2
(45) Date of Patent: Dec. 29, 2020

(54) ***DAHLIA* PLANT NAMED 'BKDAMFPBC'**

(50) Latin Name: *Dahlia hybrida*
Varietal Denomination: BKDAMFPBC

(71) Applicant: Annie Cornelia Beekenkamp, Maasdijk (NL)

(72) Inventor: Annie Cornelia Beekenkamp, Maasdijk (NL)

(73) Assignee: BEEKENKAMP PLANTS B.V., Maasdijk (NL)

( * ) Notice: Subject to any disclaimer, the term of this patent is extended or adjusted under 35 U.S.C. 154(b) by 0 days.

(21) Appl. No.: 16/873,399

(22) Filed: Apr. 4, 2020

(51) Int. Cl.
*A01H 5/02* (2018.01)
*A01H 6/14* (2018.01)

(52) U.S. Cl.
USPC ..... Plt./321
CPC ..... *A01H 6/144* (2018.05)

(58) Field of Classification Search
USPC ..... Plt./321
CPC ..... A01H 6/144; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Dahlia* plant named 'BKDAMFPBC', characterized by its upright to somewhat outwardly spreading and sturdy plant habit; freely basal branching habit; dense and bushy growth habit; dark green-colored leaves; and large double-type inflorescences with light pale purple and reddish purple bi-colored ray florets.

2 Drawing Sheets

Figure 1:
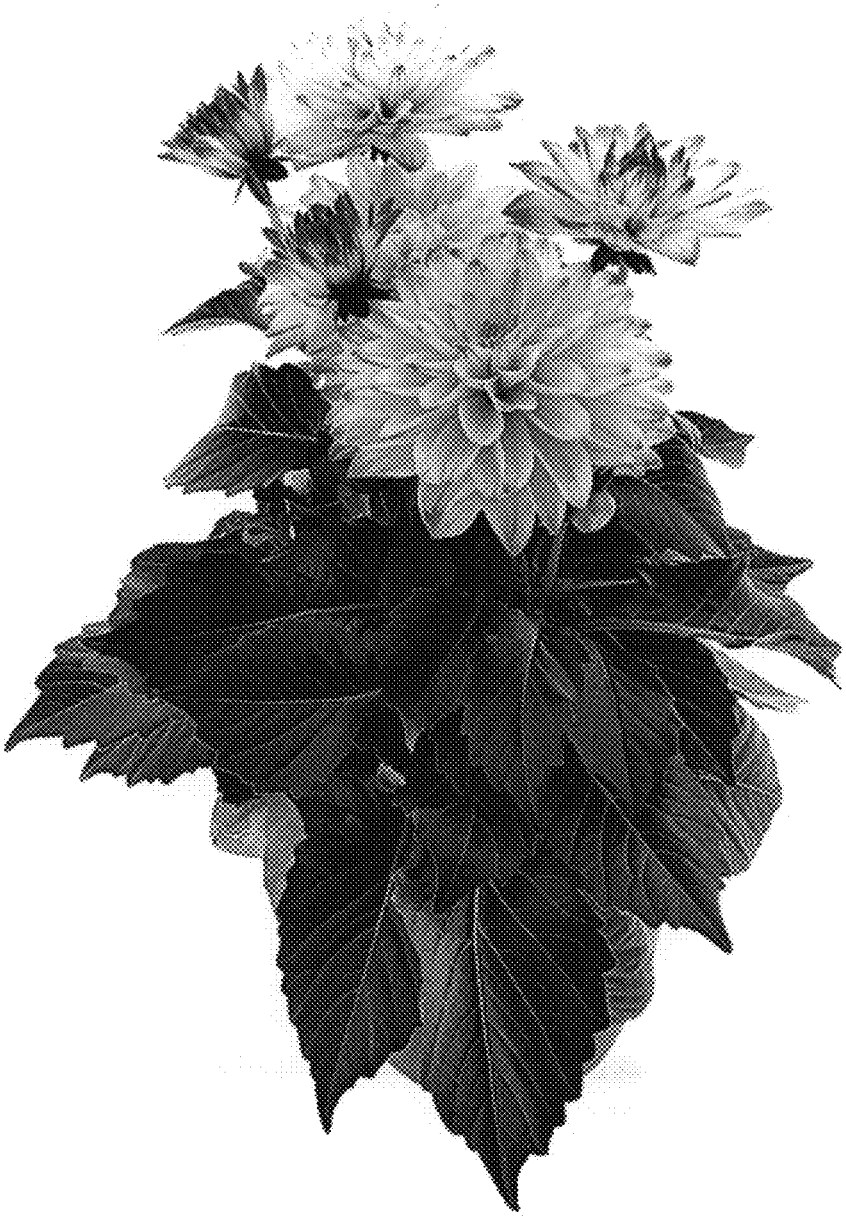

Botanical designation: *Dahlia hybrida.*
Cultivar denomination: 'BKDAMFPBC'.

BACKGROUND OF THE INVENTION

The present invention relates to a new and distinct cultivar of *Dahlia* plant, botanically known as *Dahlia hybrida* and hereinafter referred to by the name 'BKDAMFPBC'.

The new *Dahlia* plant is a product of a planned breeding program conducted by the Inventor in Maasdijk, The Netherlands. The objective of the breeding program is to create new sturdy container *Dahlia* plants that have a freely basal branching habit, and large inflorescences with attractive ray floret coloration.

The new *Dahlia* plant originated from an open-pollination in August, 2014 in Maasdijk, The Netherlands of a proprietary selection of *Dahlia hybrida* identified as code number 99-1402-01, not patented, as the female, or seed, parent with an unknown selection of *Dahlia hybrida* as the male, or pollen, parent. The new *Dahlia* plant was discovered and selected by the Inventor as a single flowering plant from within the progeny of the stated open-pollination in a controlled greenhouse environment in Maasdijk, The Netherlands in November, 2015.

Asexual reproduction of the new *Dahlia* plant by terminal cuttings in a controlled greenhouse environment in Maasdijk, The Netherlands since February, 2016 has shown that the unique features of this new *Dahlia* plant are stable and reproduced true to type in successive generations.

SUMMARY OF THE INVENTION

Plants of the new *Dahlia* have not been observed under all possible combinations of environmental conditions and cultural conditions. The phenotype may vary somewhat with variations in environmental conditions such as temperature and light intensity, without, however, any variance in genotype.

The following traits have been repeatedly observed and are determined to be the unique characteristics of 'BKDAMFPBC'. These characteristics in combination distinguish 'BKDAMFPBC' as a new and distinct *Dahlia* plant:

1. Upright to somewhat outwardly spreading and sturdy plant habit.
2. Freely basal branching habit; dense and bushy growth habit.
3. Dark green-colored leaves.
4. Large double-type inflorescences with light pale purple and reddish purple bi-colored ray florets.

Plants of the new *Dahlia* differ primarily from plants of the female parent selection in the following characteristics:

1. Plants of the new *Dahlia* are smaller than plants of the female parent selection.
2. Plants of the new *Dahlia* have light pale purple and reddish purple bi-colored ray florets whereas plants of the female parent selection have white-colored ray florets.

Plants of the new *Dahlia* can be compared to plants of *Dahlia variabilis* 'Fidahflo', disclosed in U.S. Plant Pat. No. 23,203. In side-by-side comparisons, plants of the new *Dahlia* differ from plants of 'Fidahflo' in the following characteristics:

1. Plants of the new *Dahlia* have larger inflorescences than plants of 'Fidahflo'.
2. Inflorescences of plants of the new *Dahlia* are double-types whereas inflorescences of plants of 'Fidahflo' are semi-double-types.

BRIEF DESCRIPTION OF THE PHOTOGRAPHS

The accompanying photographs illustrate the overall appearance of the new *Dahlia* plant showing the colors as true as it is reasonably possible to obtain in colored reproductions of this type. Colors in the photographs may differ slightly from the color values cited in the detailed botanical description which accurately describe the colors of the new *Dahlia* plant.

The photograph on the first sheet (FIG. 1 of 2) is a side perspective view of a typical flowering plant of 'BKDAMFPBC' grown in a container.

Figure 2:
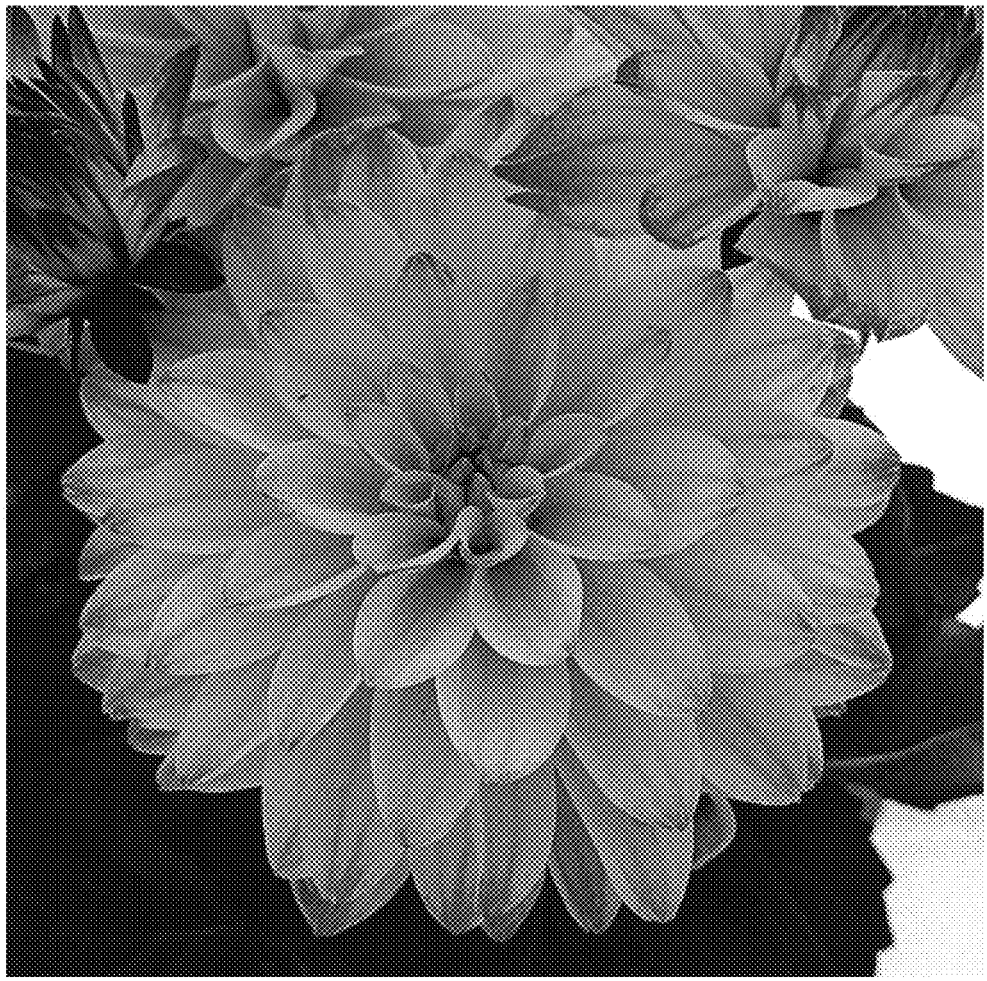

The photograph on the second sheet (FIG. 2 of 2) is a close-up view of typical inflorescences of 'BKDAMFPBC'.

DETAILED BOTANICAL DESCRIPTION

The aforementioned photographs and the following observations and measurements describe plants grown during the autumn in 11-cm containers in a glass-covered greenhouse in Maasdijk, The Netherlands and under cultural practices typical of commercial *Dahlia* production. During the production of the plants, day and night temperatures ranged from 17° C. to 19° C. Plants were pinched one time and were nine weeks from planting rooted cuttings when the photographs and description were taken. In the following description, color references are made to The Royal Horticultural Society Colour Chart, 2015 Edition, except where general terms of ordinary dictionary significance are used.

Botanical classification: *Dahlia hybrida* 'BKDAMFPBC'.

Parentage:

*Female, or seed, parent*.—Proprietary selection of *Dahlia hybrida* identified as code number 99-1492-01, not patented.

*Male, or pollen, parent*.—Unknown selection of *Dahlia hybrida*, not patented.

Propagation:

*Type*.—By terminal cuttings.

*Time to initiate roots, summer*.—About 16 days at temperatures ranging from 18° C. to 21° C.

*Time to initiate roots, winter*.—About 19 days at temperatures ranging from 19° C. to 21° C.

*Time to produce a rooted young plant, summer*.—About 21 days at temperatures ranging from 18° C. to 21° C.

*Time to produce a rooted young plant, winter*.—About 23 days at temperatures ranging from 19° C. to 21° C.

*Root description*.—Medium in thickness, fibrous; typically creamy white to light brown in color, actual color of the roots is dependent on substrate composition, water quality, fertilizers, substrate temperature and physiological age of roots; tuber development has not been observed on plants of the new *Dahlia*.

*Rooting habit*.—Moderately freely branching; medium density.

Plant description:

*Plant and growth habit*.—Upright to somewhat outwardly spreading plant habit; overall plant shape, flattened globular; sturdy plant habit; freely basal branching habit with about six primary branches developing per plant; inflorescences held above the foliar plane on strong peduncles; bushy and dense growth habit; pinching is not required but will improve branching habit; moderately vigorous growth habit and low to moderate growth rate.

*Plant height, soil level to top of foliar plane*.—About 14 cm.

*Plant height, soil level to top of floral plane*.—About 20.7 cm.

*Plant diameter or spread*.—About 28.7 cm.

*Lateral branches*.—Length: About 7 cm. Diameter: About 7 mm. Internode length: About 1.3 cm. Aspect: Primary branches are about 30° from vertical; secondary branches are about 35° from primary branch axis. Strength: Moderately strong to strong. Texture and luster: Smooth, glabrous; glossy. Color, developing: Close to 144A. Color, developed: Close to 146B; at the internodes, close to 145A to 145B.

Leaf & leaflet description:

*Arrangement*.—Leaves opposite and compound with three leaflets.

*Length, leaf*.—About 12.7 cm.

*Width, leaf*.—About 13.2 cm.

*Length, terminal leaflets*.—About 11.7 cm.

*Width, terminal leaflets*.—About 7.8 cm.

*Length, lateral leaflets*.—About 5.8 cm.

*Width, lateral leaflets*.—About 4 cm.

*Shape, leaves*.—Broadly ovate in outline.

*Shape, leaflets*.—Ovate to elliptic.

*Apex, leaflets*.—Apiculate.

*Base, leaflets*.—Attenuate.

*Margin, leaflets*.—Coarsely serrate.

*Venation pattern, leaflets*.—Pinnate.

*Texture and luster, upper surface, leaflets*.—Smooth, glabrous; slightly velvety; moderately glossy.

*Texture and luster, lower surface, leaflets*.—Smooth, sparse to moderate pubescence along veins and margins; slightly glossy.

*Color*.—Developing leaflets, upper surface: Close to NN137A. Developing leaflets, lower surface: Close to 147B. Fully expanded leaflets, upper surface: Close to between 147A and N189A; venation, close to 146A. Fully expanded leaflets, lower surface: Close to 191A; venation, close to 147B.

*Petioles*.—Length: About 2.7 cm. Diameter: About 4.5 mm by 5 mm. Strength: Moderately strong. Texture and luster, upper and lower surfaces: Smooth, glabrous; glossy. Color, upper surface: Close to 144A; distally, tinged with close to 183A. Color, lower surface: Close to 146B.

Inflorescence description:

*Appearance and arrangement*.—Large double-type inflorescences with ray and disc florets forming acropetally on a receptacle; inflorescences positioned above and beyond the foliar plane on strong peduncles; inflorescences face mostly upright to slightly outwardly; freely flowering habit with about twelve developing and fully developed inflorescences per plant at one time.

*Fragrance*.—None detected.

*Flowering response and flowering period*.—Early flowering habit, plants begin flowering about 60 days after planting; plants flower continuously during the autumn into the winter in The Netherlands.

*Post-production longevity*.—Inflorescences maintain good substance for about ten days on the plant; inflorescences persistent.

*Inflorescence buds*.—Height: About 1.6 cm. Diameter: About 1.8 cm. Shape: Flattened globular; involucral bracts moderately reflexed. Texture and luster: Smooth, glabrous; glossy. Color: Close to N144B; proximally, close to 143B; distally, tinged with close to 64B; involucral bracts, close to NN137B.

*Inflorescence size*.—Diameter: About 9 cm. Depth (height): About 5.6 cm. Disc diameter: About 8 mm; typically inconspicuous.

*Receptacles*.—Height: About 5 mm. Diameter: About 9 mm. Shape: Lunate. Color: Close to 146D.

*Ray florets*.—Quantity per inflorescence and arrangement: About 110 arranged in about six whorls. Length: About 4 cm. Width: About 1.6 cm. Shape: Oblanceolate, concave. Apex: Acute to shallowly praemorse. Base: Attenuate. Margin: Entire. Aspect: Initially upright to slightly upright to close to horizontal and eventually slightly downward. Texture and luster, upper and lower surfaces: Smooth, glabrous; velvety; matte. Color: When opening, upper surface: Close to 155A; towards the apex, close to N74A; at the base, close to 5C. When opening, lower surface: Close to between 155A and 158D; towards the apex, close to N74B; at the base, close to 2C. Fully opened, upper surface: Close to 76D; towards the apex, close to N74A; at the base, close to 5C; venation, close to N74B to N74C; color does not change with development. Fully opened, lower surface: Close to 76D; towards the apex, close to NN74B; at the base, close to 5D; venation, close to NN74B to NN74C; color does not change with development.

*Disc florets*.—Quantity per inflorescence and arrangement: About 35 massed at the center of the inflorescence in about five spiral whorls; typically inconspicuous. Length: About 6 cm. Diameter: About 8 mm. Shape: Tubular, elongated; apices, acute. Texture and luster, inner and outer surfaces: Smooth, glabrous; glossy. Color, when opening, inner and outer surfaces: Apex: Close to 13A. Mid-section and base: Close to 151D. Color, fully opened, inner and outer surfaces: Apex: Close to 12A. Mid-section and base: Close to 154B.

*Phyllaries*.—Quantity per inflorescence and arrangement: About eight arranged in a single whorl. Length: About 1.3 cm. Width: About 8 mm. Shape: Obovate. Apex: Acute. Base: Cuneate. Margin: Entire. Texture and luster, upper and lower surfaces: Smooth, glabrous; glossy. Color, upper surface: Close to NN137A. Color, lower surface: Close to NN137B.

*Peduncles*.—Length, terminal peduncle: About 7.9 cm. Diameter, terminal peduncle: About 3 mm. Strength: Strong. Texture and luster: Smooth, glabrous; moderately glossy. Color: Close to between 177A and N199B; distally, close to 144A.

*Reproductive organs*.—Androecium, present on disc florets only: Quantity per floret: About five. Filament length: About 3 mm. Filament color: Close to 157D. Anther length: About 4.5 mm. Anther shape: Narrowly oblong. Anther color: Close to 23B. Pollen amount: Moderate. Pollen color: Close to 23A. Gynoecium, present on disc florets only: Quantity per floret: One. Pistil length: About 1 cm. Style length: About 8 mm. Style color: Close to 150C; distally, close to 21C. Stigma diameter: About 8 mm. Stigma shape: Cleft. Stigma color: Close to 23A. Ovary color: Close to 150C. Seeds and fruits: To date, seed and fruit development have not been observed on plants of the new *Dahlia*.

Pathogen & pest resistance: To date, plants of the new *Dahlia* have not been observed to be resistant to pathogens and pests common to *Dahlia* plants.

Temperature tolerance: Plants of the new *Dahlia* have been observed to tolerate high temperatures of about 35° C. and to be suitable for USDA Hardiness Zones 9 to 11.

It is claimed:

1. A new and distinct *Dahlia* plant named 'BKDAMF-PBC' as illustrated and described.

* * * * *